United States Patent [19]
Young

[11] 4,345,596
[45] Aug. 24, 1982

[54] ARTERIAL CATHERIZATION DEVICE

[75] Inventor: Ruperto S. Young, Amsterdam, N.Y.

[73] Assignees: Janis Marie Young, Amsterdam; Roberta H. Wessendorf, Guilderland, both of N.Y.

[21] Appl. No.: 333,704

[22] Filed: Dec. 23, 1981

[51] Int. Cl.³ .............................................. A61M 5/00
[52] U.S. Cl. ................................. 128/214 R; 128/345; 128/349 R; 128/DIG. 16
[58] Field of Search ................ 128/214, 214.2, 214.4, 128/213, 220, 221, 303, 303.11, 303.18, 329, 341, 343, 345, 347, 348, 349, DIG. 9, DIG. 16, DIG. 26

[56] References Cited
U.S. PATENT DOCUMENTS

| | | | |
|---|---|---|---|
| 1,559,737 | 11/1925 | Bock | 128/345 |
| 2,566,499 | 9/1951 | Richter | 128/221 |
| 2,842,133 | 7/1958 | Uhma | 128/345 |
| 3,330,278 | 7/1967 | Santomieri | 128/214.4 |
| 3,568,660 | 3/1971 | Chambers et al. | 128/2 |
| 3,610,239 | 10/1971 | Huggins | 128/214.4 |
| 3,677,244 | 7/1972 | Hassinger | 128/214.4 |
| 3,704,712 | 11/1972 | Giesy et al. | 128/345 |
| 4,147,165 | 4/1979 | Taushinski | 128/214.4 |

Primary Examiner—Stephen C. Pellegrino
Attorney, Agent, or Firm—Walter F. Wessendorf, Jr.

[57] ABSTRACT

Disclosed is a surgical instrument for insertion into a blood-vessel lumen and comprises a separable assembly of longitudinal sections in mating relationship having tube and hub sections. Twisting movement of lateral separator tabs integral with the proximal ends of the hub sections effects relative movement to initially unlock releasable interdigitation locking means which the tube sections incorporate distally, and which the hub sections incorporate both distally and proximally, with such continued relative movement causing biased interfaces on the hub sections to cam open and force apart the longitudinal sections.

21 Claims, 8 Drawing Figures

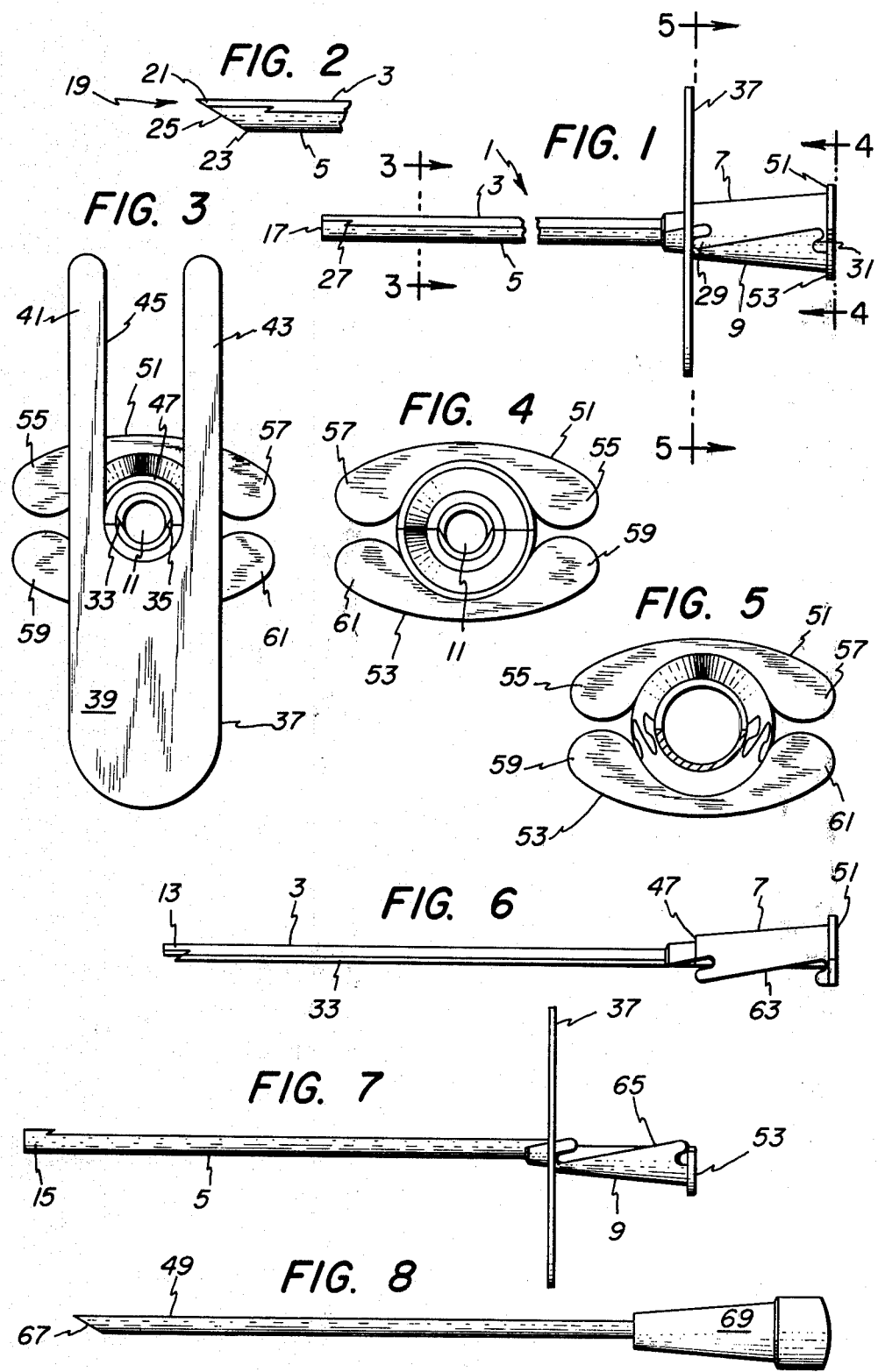

ARTERIAL CATHERIZATION DEVICE

BACKGROUND OF THE INVENTION

1. Technical Field

This invention relates to arteriograms and arterial catheterizations for therapeutic procedures and, in particular, relates to a surgical instrument embodied as an arterial needle or as a cannula for specific use in such procedure for insertion into the lumen of a blood vessel.

2. Background Art

The prior art, U.S. Pat. No. 2,566,499 relates to an expansile surgical needle; U.S. Pat. No. 2,842,133 relates to a surgical or medical vein dilating device; U.S. Pat. No. 3,330,278 relates to a hypodermic needle for a cannula placement unit; U.S. Pat. No. 3,568,660 relates to a pacemaker catheter; U.S. Pat. No. 3,610,239 relates to a detachable hollow guide needle; U.S. Pat. No. 3,677,244 relates to a removable catheter needle; U.S. Pat. No. 4,147,165 relates to a separable needle for inserting a catheter into the blood stream.

The immediate operating site is defined as being above the plane of the operating table with the patient lying on his back on such operating table. Physical access to the immediate operating site is limited to one lateral side of the operating table because the other lateral side of the operating table is spatially occupied by x-ray equipment and other monitoring equipment disposed above the plane of the operating table. Since access to the patient is limited to one lateral side of the operating table, only two persons can physically occupy and function on that "free" lateral side of the operating table. These two persons are the surgeon and his assistant. Since the surgeon wants to and must maintain by himself full and complete physical control at all times of the surgical procedure being performed, the surgeon does not want his assistant physically involved in the surgical procedure being performed other than in handing the surgeon instruments, etc. or otherwise in performing such tasks as so directed by the surgeon. Moreover, the immediate operating site is cluttered with tubing, wiring, and the like, associated with such equipment. The old saying of too many cooks spoil the broth applies. More than two persons participating at the immediate operating site results in their physical interference with one another and with the surgical procedure being performed, as well as rendering the maintenance of sterility difficult if not impossible. This explanation of the prior-art problems with respect to the immediate operating site points up the need for the surgical instrument of this invention embodied as a surgical needle or embodied as a cannula which the surgeon himself can insert into the lumen of the blood vessel that has been penetrated and which surgical instrument the surgeon by himself can thereafter withdraw and remove with one hand from such blood vessel, remove with one hand from the patient's body, and thereupon with one twisting movement of his one hand break apart and discard—while with his other free hand maintaining compression on the puncture site to prevent bleeding and hematoma formation.

Arteriograms and arterial catherizations for therapeutic procedures include the following sequence of maneuvers: (1) penetrating the blood vessel with a surgical instrument such as an arterial needle or a cannula employing a stylet; (2) disposing such surgical needle or cannula into the arterial lumen; (3) threading a long guide wire through the needle or cannula into the arterial lumen; (4) removing the arterial needle or cannula from the artery and patient's body, and sliding the arterial needle or cannula out of the proximal end of the guide wire, leaving the guide wire in the arterial lumen; (5) introducing a blood vessel dilator proximally along the guide wire and distally into the arterial lumen to enlarge the puncture hole for subsequent catheterization; (6) removal of the dilator from the artery and sliding it proximally along and out of the guide wire; (7) introducing the catheter over the guide wire proximally and then sliding same distally over such guide wire and into the arterial lumen; (8) removing the guide wire proximally and leaving the emplaced catheter for examination or therapeutic purposes.

In the arterial system, blood flows under high pressure. Therefore, once the arterial wall is punctured, continuous compression on the punctured site is critical to prevent bleeding and hematoma formation. Such continuous compression is accomplished by the surgeon's application of finger pressure, thereby leaving the surgeon with only his other hand to manipulate the surgical instrument of this invention embodied as an arterial needle or as a cannula to withdraw such surgical instrument from the patient's artery, to remove such surgical instrument from the patient's body, and to thereupon break same apart with an applied twisting motion of that other hand and to discard same. Therefore, such a surgical instrument that can be broken apart by applied twisting motion of one hand is essential.

When a guide wire is in the arterial lumen, blood clots will start forming around such emplaced guide wire. These clots can result in blockage of the artery and possibly can lead to loss of an organ or extremity, or necessitate a second surgical procedure for the removal of such clot. Hence, the faster the emplaced is removed, the lesser will be the chance of such described complications. Since the surgical instrument of this invention can be easily and quickly broken apart by twisting motion applied by one hand, a great deal of time is saved because the arterial needle or cannula does not have to be slid along the entire length of the guide wire to the proximal end of such guide wire to effect the removal of such arterial needle or cannula, but can be simply removed from the blood vessel and broken apart. Additional time is saved for the reason that the guide wire does not have to be sterilized after removing and breaking apart such arterial needle or cannula in comparison to the prior-art requirement for such sterilization of the guide wire. In the prior art, with the removal of such surgical needle from the proximal end of the guide wire, the guide wire becomes bacterially contaminated with blood. Accordingly, such guide wire must be sterilized before the blood vessel dilator or the catheter is introduced proximally over such guide wire and then distally into the arterial lumen. Such ability of the surgeon to break away the arterial needle or cannula with one hand permits such surgeon's assistant to be employed in threading the catheter, in regulating the infusion of material, in preparing the equipment for sequential study or treatment, and in maintaining the sterile operating field.

The integral locking mechanism incorporated in this invention's surgical instrument is important in maintaining needle or cannula integrity without leakage of blood for the reason that arteries are deep structures with blood flow under high pressure, and tissue and artery penetration must be accomplished without loss of such integrity.

Accordingly, the object of the invention is to contribute to the solution of the discussed problems of the prior art by providing the surgical instrument of this invention embodied as an arterial needle or as a cannula which the surgeon with one hand can controllably insert into the arterial lumen, can thereafter controllably withdraw with the same hand therefrom and thereupon with the same hand break apart and discard such surgical instrument.

SUMMARY OF THE INVENTION

In accordance with the invention, there is provided a surgical instrument embodied as an arterial needle or as a cannula comprising two semicircular metallic upper and lower tube halves, made of stainless steel or other material suitable for such surgical use and which can be sterilized, that are integral with respective upper and lower hub halves, made of any kind of plastic material that is suitable for surgical use and which can be sterilized. When assembled, the tube halves mate along the longitudinal axis forming thereby a hollow tube having thereby a lumen. The hub halves similarly mate with the resulting hub assembly having an open cylindrical configuration tapered outward proximally, in communication with such hollow-tube lumen. The distal ends of the assembled tube halves define a blunt, round and non-cutting tip in the cannula embodiment of the surgical instrument of this invention. The distal ends of the assembled tube halves are beveled and define a piercing point in the arterial needle embodiment of the surgical instrument of this invention.

Distally, the assembled tube halves have interdigitation locking means. Distally and proximally, the hub assembly has interdigitation locking means. Such interdigitation locking means cooperate to maintain the longitudinal beveled interfaces of the upper and lower tube halves in air and leak-proof relationship.

The distal portion of the lower hub half has fixed therewith in transverse relationship a laterally extending flat finger grip of such similar suitable plastic material. Such finger grip permits the surgeon to dispose his index and middle fingers of one hand around the posterior surface of such finger grip and to dispose his thumb of the same hand over the proximal end of the hub assembly. The manipulative position of the surgeon's index and middle fingers, and his thumb, is similar to the manipulative position of the index and middle fingers, and thumb, when a human operator wants to effect a plunger action on an instrument or device. The functional purpose of the finger grip is to allow controlled manipulation of the cannula with its assembled stylet or arterial needle for arterial puncture, to allow controlled maneuvering for insertion of the cannula or arterial needle into the arterial lumen, and to allow controlled removal from the artery.

The upper and lower hub halves structurally incorporate separator tabs that laterally extend from the proximal ends of such hub halves. After removal of the arterial needle or cannula from the artery, same is broken apart into its constituent longitudinal sections or halves and discarded. To effect such separation, the surgeon engages his thumb with the anterior surface of a separator tab integral with the lower hub half, engages his index finger with the posterior surface of the separator tab integral with the upper hub half and on the same lateral side as the other separator tab, and, with his index finger and thumb of his one hand so manipulatively engaged, effects a twisting motion in such direction that the lower tube half will be moved longitudinally relative to the upper tube half. Such movement will unlock all three interdigitation locking means; and since the upper and lower hub halves have interfaces on the bias or diagonally, such movement of the lower tube half relative to the upper tube half will cam open and force apart the upper and lower tube halves once the interdigitation locking means have been unlocked. The interfaces of the upper hub half function as the cam and the interfaces of the lower hub half function as the follower. As the relative movement of the upper and lower tube halves increases, the camming effect of the diagonal interfaces of the upper and lower hub halves is more pronounced.

BRIEF DESCRIPTION OF THE DRAWINGS

The object of the invention and other objects of the invention should be discerned and appreciated by reference to the drawings, wherein like reference numerals refer to similar parts throughout the several views, in which:

FIG. 1 is a view of the embodied cannula of this invention;

FIG. 2 is a view of the distal portion of the embodied arterial needle of this invention;

FIG. 3 is an enlarged view taken in the direction of the arrows 3—3 in FIG. 1;

FIG. 4 is an enlarged view taken in the direction of the arrows 4—4 in FIG. 1;

FIG. 5 is an enlarged view taken in the direction of the arrows 5—5 in FIG. 1;

FIG. 6 is a view of the upper half of the cannula embodiment of this invention;

FIG. 7 is a view of the lower half of the cannula embodiment of this invention; and FIG. 8 is a view of the stylet employed with the cannula embodiment of this invention.

DESCRIPTION OF THE PREFERRED EMBODIMENT

In FIG. 1 of the drawings, reference numeral 1 generally refers to the cannula embodiment of this invention. Cannula 1 comprises semicircular metallic, upper and lower tube halves 3 and 5, integral with two respective upper and lower hub halves 7 and 9. When assembled, the tube halves 3 and 5 unite and mate along the longitudinal axis forming a hollow tube having a lumen 11. The two hub halves 7 and 9 mate with the hub assembly resulting thereby being of open cylindrical configuration tapered outward proximally and in communication with the lumen 11. The distal ends 13 and 15 of the assembled tube halves 3 and 5 define a blunt, round and non-cutting tip 17.

In the arterial needle embodiment of this invention, shown in FIG. 2 and generally referred to by reference numeral 19, the upper and lower distal ends 21 and 23 have common beveled edges defining a piercing point 25. All of the structure incorporated in the cannula embodiment 1 is similarly incorporated in the arterial needle embodiment 19, with the only structural difference being that the upper and lower tube halves 3 and 5 have respective beveled distal ends 21 and 23 defining such piercing point 25.

Distally, the assembled tube has releasable interdigitation locking means 27, as shown. Distally and proximally, the hub assembly has releasable interdigitation locking means 29 and 31, as shown. Such interdigitation locking means 27, 29 and 31 cooperate to maintain the beveled interfaces 33 and 35 of the respective upper and lower tube halves 3 and 5 in air and leak-proof relationship. It should be noted that in FIG. 3 of the drawings the upper and lower tube halves 3 and 5 are not shown in section because to apply cross hatching thereto would obscure the important structural features of the beveled interfaces 33 and 35.

The distal portion of the lower hub half 9 has fixed therewith in transverse relationship a laterally extending flat finger grip 37 comprising a solid wing member 39 and bifurcated wing elements 41 and 43 defining an elongated clearance slot 45. The distal portion of the upper hub half 7 has a shoulder portion 47 functioning as a limit stop against which the anterior surfaces of the wing elements 41 and 43 abut. The finger grip 37 permits the surgeon to dispose and position his index and middle fingers around the posterior surface of the finger grip 37 and dispose his thumb over the proximal end of the hub assembly. The manipulative position of the surgeon's index and middle fingers, and his thumb, is similar to the manipulative position of the index and middle fingers, and thumb, when a human operator wants to effect a plunger-type action with reference to a device or instrument. The functional purpose of the finger grip 37 is to allow controlled manipulation of the arterial needle or cannula with its assembled stylet 49 for arterial puncture, for controlled maneuvering for insertion of the needle or cannula into the arterial lumen, and for controlled removal from the artery.

Integral with the laterally extending from the proximal ends of the upper and lower hub halves 7 and 9 are respective upper and lower separators 51 and 53. After the arterial needle or cannula is removed from the artery and slid proximally along the guide wire a short and sufficient distance to assure that same is completely free of the tissue and puncture site, same is broken apart into its separate longitudinal halves and discarded. As viewed in FIG. 4, the upper separator 51 has upper right and left separator tabs 55 and 57; and lower separator 53 has lower right and left separator tabs 59 and 61. Assuming the surgeon is right-handed: to effect such separation, the surgeon engages his right thumb with the anterior surface of the lower right separator tab 59, engages his right index finger with the posterior surface of the upper right separator tab 55, and with his right thumb and index finger so appropriately engaged, manipulatively effects a twisting motion downwardly, as viewed in FIG. 4, such that the lower tube half 5 will be moved to its left, as viewed in FIG. 1, relative to upper tube 3 to thereby release the three interdigitation locking means 27, 29 and 31. Since the respective interfaces 63 and 65 of the upper and lower hub halves 7 and 9 are on the bias or diagonally, such longitudinal movement of the lower tube half 5 relative to the upper tube half 3 will cam open and thereby force apart the upper and lower tube halves 3 and 5 once and upon the interdigitation means 27, 29 and 31 have been unlocked. In such camming movement, the interfaces 63 of the upper hub half 7 would function as the cam and the interfaces 65 of the lower hub half 9 would function as the follower. As the relative longitudinal movement of the upper and lower tube halves increases, the camming effect of the coacting interfaces 63 and 65 is more pronounced to spring apart the upper and lower tube halves 3 and 5. As viewed in FIG. 1, lower tube half 5 would be forced to spring apart in a downward direction with the elongated clearance slot 45 clearing the upper tube half 3 and dropping away.

Of course, if the surgeon is left-handed, he would employ his left thumb and index finger to effect such twisting motion by appropriate manipulative engagement with the upper left separator tab 57 and lower left separator tab 61.

When the cannula is employed, same is assembled with stylet 49. Stylet 49 has a shank portion of stainless steel or other suitable material having a beveled, sharp-cutting tip 67 on its distal end and an end plug 69 fixed on the proximal end. The cannula complementally receives stylet 49 such that its tip 67 extends slightly beyond the blunt, round and non-cutting tip 17 in order that such sharp-cutting tip 67 can penetrate the skin, tissue and arterial wall to introduce the non-cutting tip 17 therein followed by removal of the stylet 49 from the cannula 1 and subsequent appropriate maneuvering of the cannula's non-cutting tip 17 for insertion into the arterial lumen. In assembly, the lumen 11 of the cannula 1 complementally receives therein the shank portion of such stylet 49 and the tapered open cylindrical configuration of the hub assembly complementally receives the tapered end plug 69. End plug 69 similarly is made of such suitable plastic material employed for the hub halves 7 and 9.

Of course when the arterial needle 19 is employed, its piercing point 25 is appropriately disposed to penetrate the skin, tissue and arterial wall followed by sufficient withdrawal to permit appropriate subsequent maneuvering of the distal end of such arterial needle for insertion of same into the arterial lumen.

Having thusly described my invention, I claim:

1. A surgical instrument for insertion into a blood-vessel lumen, said surgical instrument comprising a separable assembly of longitudinal sections in mating relationship, said longitudinal sections having first cooperating releasable interdigitation locking means for maintaining said longitudinal sections in their assembled relationship and releasable upon relative movement of said longitudinal sections, said longitudinal sections having second means cooperating to force apart and separate said longitudinal sections by further relative movement of said longitudinal sections.

2. A surgical instrument in accordance with claim 1, wherein said longitudinal sections comprise tube sections.

3. A surgical instrument in accordance with claim 1, wherein said longitudinal sections comprise hub sections.

4. A surgical instrument in accordance with claim 1, wherein said longitudinal sections comprise tube sections defining a hollow tube having a lumen.

5. A surgical instrument in accordance with claim 1, wherein said longitudinal sections comprise hub sections defining a hub assembly of open cylindrical configuration.

6. A surgical instrument in accordance with claim 1, wherein said longitudinal sections comprise tube sections having distal ends and wherein said distal ends define a blunt, round and non-cutting tip.

7. A surgical instrument in accordance with claim 1, wherein said longitudinal sections comprise tube sections having distal ends and wherein said distal ends have common beveled edges defining a piercing point.

8. A surgical instrument in accordance with claim 1, wherein said longitudinal sections comprise tube sections having beveled interfaces, wherein said locking means cooperate to maintain said beveled interfaces of said tube sections in air and leak-proof relationship.

9. A surgical instrument in accordance with claim 1, wherein said surgical instrument has a finger grip means to allow controlled manipulation of said surgical instrument for insertion into the blood-vessel lumen and for controlled removal therefrom.

10. A surgical instrument in accordance with claim 1, wherein said surgical instrument has separating means and wherein manipulative twisting motion applied to said separating means effects relative movement of said longitudinal sections to release said locking means.

11. A surgical instrument in accordance with claim 1, wherein said second means comprises interfaces on the bias such that such relative movement of said longitudinal sections cams open and thereby forces apart said longitudinal sections.

12. A surgical instrument in accordance with claim 1, wherein said longitudinal sections comprise hub sections having said second means and wherein said second means comprises interfaces on the bias such that such relative movement of said longitudinal sections cams open and thereby forces apart said longitudinal sections.

13. A surgical instrument in accordance with claim 1, wherein said longitudinal sections comprise tube sections and wherein said tube sections distally have said locking means.

14. A surgical instrument in accordance with claim 1, wherein said longitudinal sections comprise hub sections and wherein said hub sections distally and proximally have said locking means.

15. A surgical instrument in accordance with claim 1, wherein said longitudinal sections comprise tube sections and hub sections, wherein said tube sections distally have said locking means and wherein said hub sections distally and proximally have said locking means.

16. A surgical instrument in accordance with claim 1, wherein said longitudinal sections comprise tube sections and hub sections, wherein said tube sections define a hollow tube having a lumen, wherein said hub sections define a hub assembly of open cylindrical configuration in communication with said hollow-tube lumen.

17. A surgical instrument in accordance with claim 1, wherein said longitudinal sections comprise tube sections and hub sections, wherein said tube sections distally have said locking means, wherein said hub sections distally and proximally have said locking means, wherein said tube sections have beveled interfaces and wherein said locking means cooperate to maintain said beveled interfaces of said tube sections in air and leak-proof relationship.

18. A surgical instrument in accordance with claim 1, wherein said longitudinal sections comprise hub sections having said second means, said second means comprising interfaces on the bias such that such relative movement of said longitudinal sections cams open and thereby forces apart said longitudinal sections, wherein said surgical instrument has separating means and wherein manipulative twisting motion applied to said separating means effects such relative movement of said longitudinal sections.

19. A surgical instrument in accordance with claim 1, wherein said longitudinal sections comprise tube sections and hub sections, wherein said tube sections define a hollow tube having a lumen, wherein said hub sections define a hub assembly of open cylindrical configuration in communication with said hollow-tube lumen, wherein said tube sections distally have said locking means, wherein said hub sections distally and proximally have said locking means, wherein said tube sections have beveled interfaces, wherein said locking means cooperate to maintain said beveled interfaces of said tube sections in air and leak-proof relationship, wherein said hub sections have said second means, said second means comprising interfaces on the bias such that relative movement of said longitudinal sections cams opens and thereby forces apart said longitudinal sections, wherein said surgical instrument has separating means and wherein manipulative twisting motion applied to said separating means effects such relative movement of said longitudinal sections.

20. A surgical instrument in accordance with claim 1, wherein said surgical instrument has separating means, wherein said separating means comprises separator tabs, wherein said longitudinal sections comprise hub sections, wherein said hub sections have proximal ends, wherein said separator tabs are integral with and laterally extend from said proximal ends of said hub sections and wherein manipulative twisting motion applied to said separator tabs effects relative movement of said longitudinal sections to release and unlock said locking means.

21. A surgical instrument in accordance with claim 19, wherein said surgical instrument has separating means, wherein said separating means comprises separator tabs, wherein said hub sections have proximal ends, wherein said separator tabs are integral with and laterally extend from said proximal ends of said hub sections and wherein manipulative twisting motion applied to said said separator tabs effects relative movement of said longitudinal sections to release and unlock said locking means.

* * * * *